United States Patent
Lenherr

(10) Patent No.: US 10,940,052 B2
(45) Date of Patent: Mar. 9, 2021

(54) METHOD FOR PRODUCING A TAMPON

(71) Applicant: Ruggli Projects AG, Hagendorn (CH)

(72) Inventor: Harald Lenherr, Beringen (CH)

(73) Assignee: RUGGLI PROJECTS AG, Hagendorn (CH)

( * ) Notice: Subject to any disclaimer, the term of this patent is extended or adjusted under 35 U.S.C. 154(b) by 115 days.

(21) Appl. No.: 15/739,201

(22) PCT Filed: Jun. 22, 2016

(86) PCT No.: PCT/EP2016/064462
§ 371 (c)(1),
(2) Date: Mar. 6, 2018

(87) PCT Pub. No.: WO2016/207242
PCT Pub. Date: Dec. 29, 2016

(65) Prior Publication Data
US 2018/0185202 A1    Jul. 5, 2018

(30) Foreign Application Priority Data
Jun. 25, 2015   (AT) ............... A 50554/2015

(51) Int. Cl.
*A61F 13/22*   (2006.01)
*A61F 13/20*   (2006.01)
*A61F 13/34*   (2006.01)

(52) U.S. Cl.
CPC ........ *A61F 13/2094* (2013.01); *A61F 13/206* (2013.01); *A61F 13/2071* (2013.01); *A61F 13/34* (2013.01)

(58) Field of Classification Search
CPC .... A61F 13/20; A61F 13/202; A61F 13/2051; A61F 13/206; A61F 13/2071; A61F 13/2082; A61F 13/2085; A61F 13/2094
See application file for complete search history.

(56) References Cited

U.S. PATENT DOCUMENTS 2,926,667 A * 3/1960 Burger, Jr. .......... A61F 13/2085
                                                         604/365
4,104,127 A * 8/1978 Bucalo ................... A61B 10/02
                                                         600/582
(Continued)

FOREIGN PATENT DOCUMENTS

CA     2 085 923 A1    3/1994
DE     35 19 514 A1    12/1986
(Continued)

OTHER PUBLICATIONS

International Search Report of PCT/EP2016/064462, dated Sep. 26, 2016.
(Continued)

*Primary Examiner* — Catharine L Anderson
(74) *Attorney, Agent, or Firm* — Collard & Roe, P.C.

(57) ABSTRACT

The invention relates to a method for the manufacture of a tampon (1) having at least one absorbent body made from an absorbent material (6), the tampon (1) having a proximal end (2) and a distal end (3) and a middle part extending between the distal end and the proximal end, as well as an extraction means (5) connected to the absorbent body and situated at the distal end (3), and the tampon has a covering made from a nonwoven material (4), which, with the exception of a pass-through opening (13) for the extraction means (5), completely covers at least the distal end (3), by which the escaping of fibers at the distal end (3) is prevented, and the covering additionally forming a protection against the fluid leakage.

8 Claims, 5 Drawing Sheets

(56) References Cited

U.S. PATENT DOCUMENTS

| | | | |
|---|---|---|---|
| 4,222,381 A * | 9/1980 | Widlund | A61F 13/206 |
| | | | 604/365 |
| 5,185,010 A | 2/1993 | Brown, Jr. | |
| 7,977,532 B2 | 7/2011 | Hasse et al. | |
| 9,138,355 B2 | 9/2015 | Hasse et al. | |
| 9,610,201 B2 * | 4/2017 | Schmidt-Foerst | ........................... |
| | | | A61F 13/2028 |
| 2002/0026177 A1 | 2/2002 | Lochte et al. | |
| 2005/0096620 A1 | 5/2005 | Awolin et al. | |
| 2014/0188064 A1 | 7/2014 | Yamaki | |

FOREIGN PATENT DOCUMENTS

| | | |
|---|---|---|
| DE | 36 34 704 A1 | 4/1988 |
| DE | 9217228 U1 | 3/1993 |
| DE | 693 11 384 T2 | 1/1998 |
| DE | 197 53 665 A1 | 6/1999 |
| DE | 603 09 485 T2 | 8/2007 |
| DE | 20 2012 011 679 U1 | 2/2013 |
| EP | 1 677 722 B1 | 7/2009 |
| EP | 2 749 261 A1 | 7/2014 |
| GB | 2 010 680 A | 7/1979 |
| WO | 2004/021943 A1 | 3/2004 |
| WO | 2015/104301 A1 | 7/2015 |

OTHER PUBLICATIONS

Letter of Austrian Patent Attorney to European Patent Office in PCT/EP2016/064462, dated Aug. 22, 2017.

* cited by examiner

Fig.4
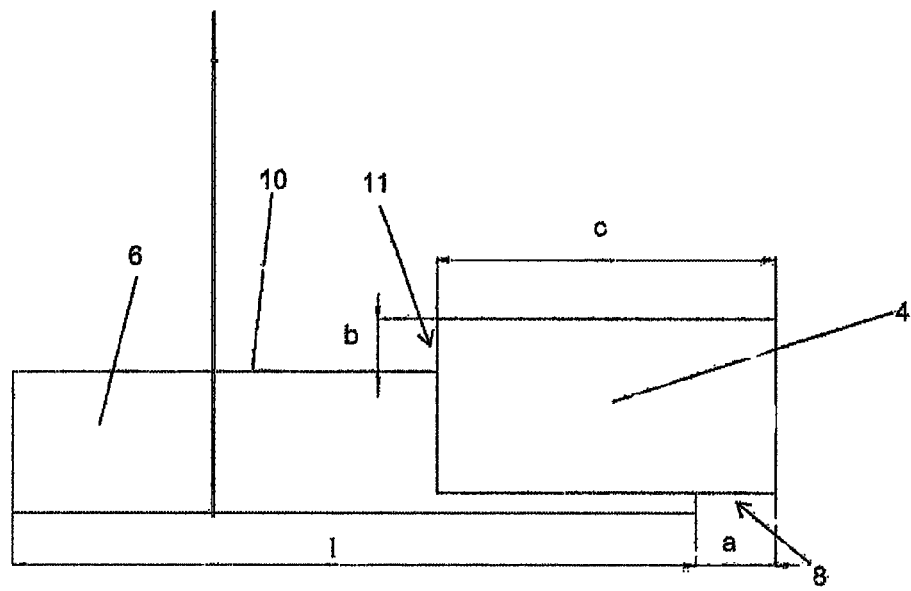
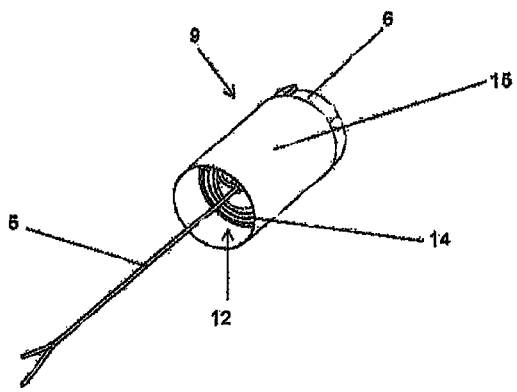
Fig.5

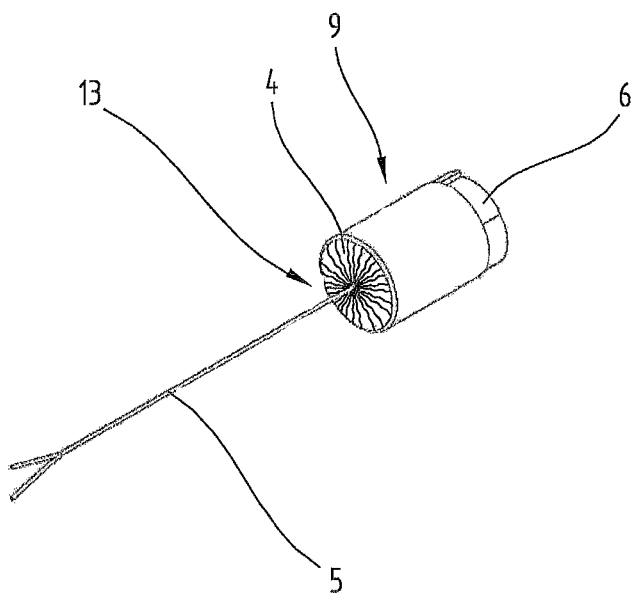
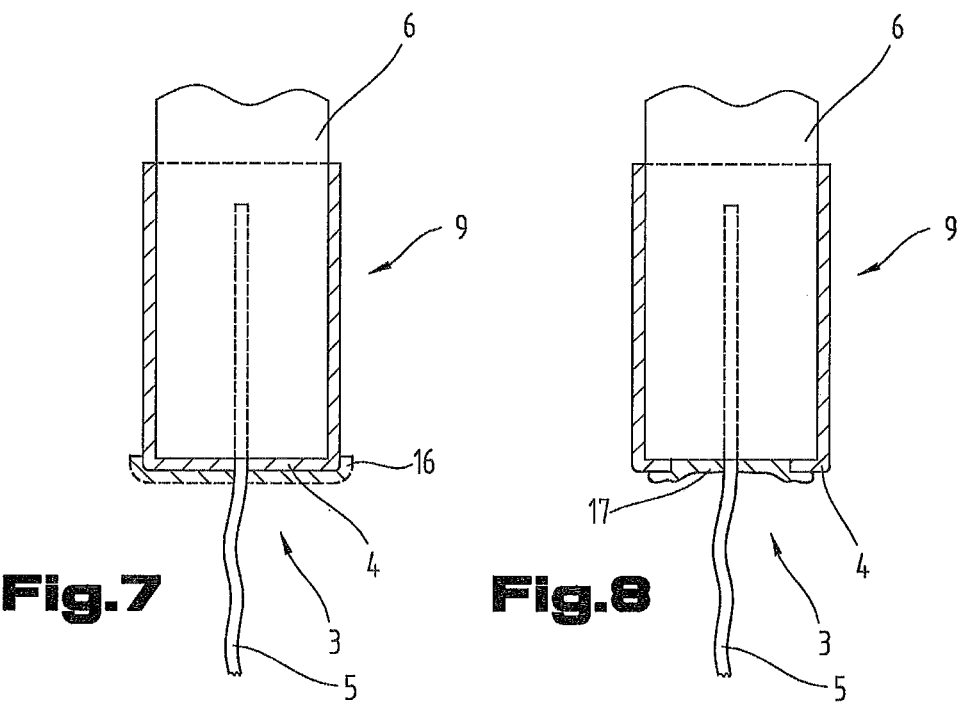

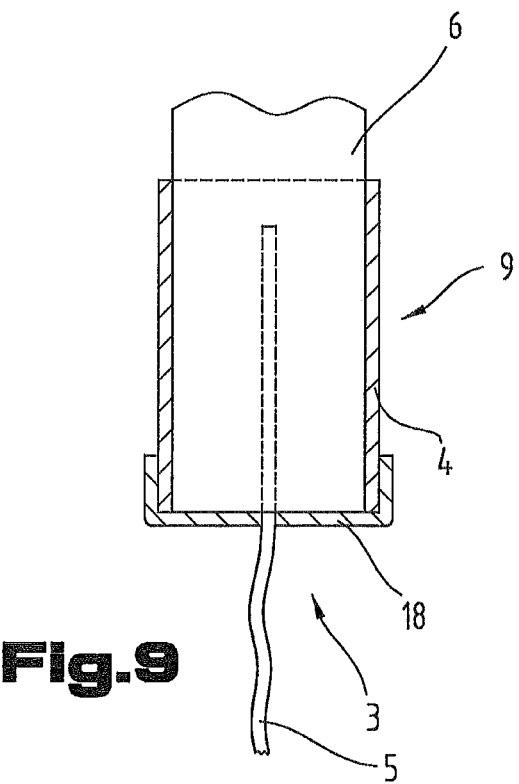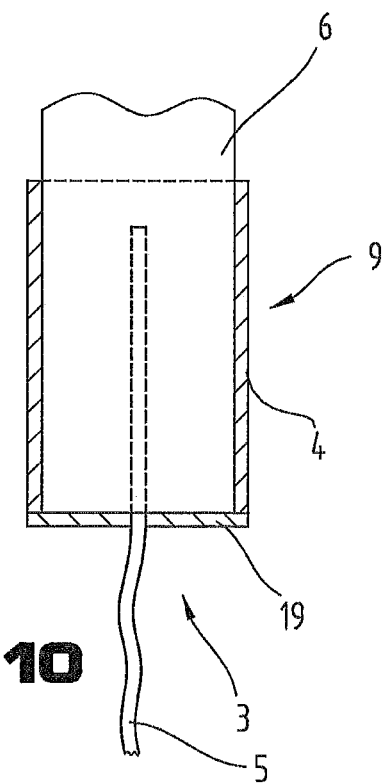

METHOD FOR PRODUCING A TAMPON

CROSS REFERENCE TO RELATED APPLICATIONS

This application is the National Stage of PCT/EP2016/064462 filed on Jun. 22, 2016, which claims priority under 35 U.S.C. § 119 of Austrian Application No. A50554/2015 filed on Jun. 25, 2015, the disclosure of which is incorporated by reference. The international application under PCT article 21(2) was not published in English.

The present invention relates to a method for the manufacture of a tampon, including the following steps:
i) positioning of a strip made from a nonwoven material on a strip made from an absorbent material so that a part of the strip made from nonwoven material protrudes over the narrow side of the strip made from absorbent material,
ii) connecting the strip made from nonwoven material to the strip made from absorbent material,
iii) situating an extraction means at the strip made from absorbent material,
iv) rolling up the strip made from absorbent material and the strip made from nonwoven material into a roll, in which the strip made from nonwoven material covers a section of the surface shell of the roll,
v) connecting the protruding part of the strip made from nonwoven material to a section of the strip made from nonwoven material connected to the strip made from absorbent material.

Furthermore, the present invention relates to a tampon having at least one absorbent body made from an absorbent material, the tampon having a proximal end and a distal end and a middle part extending between the distal end and the proximal end, and having an extraction means connected to the absorbent body and situated at the distal end.

In known tampons manufactured from a rolled strip made from absorbent material, an undesired detaching of fibers of the absorbent material at an extraction end may result during use despite the compaction of the material; this is in particular the case, when detaching the extraction means from the distal end by fingers. Since the tampon is wound up during the manufacture, there is also the danger that conventional tampons after their use or during removal (pulling at the string) "telescope" out of the body, as it is illustrated in FIG. 1, and in many cases parts of the strip made from absorbent material, for example cotton, may remain in the body.

From EP1677722B1 a tampon is known, in which a greater part of the tampon is provided with a sleeve made from a hydrophobic or watertight material. This, however, has the disadvantage of a reduced fluid intake. In other tampons, it is additionally disadvantageous that they have a smaller pass-through time for fluid, meaning the time until a drop of the fluid discharges at the distal end when saturating a tampon with a fluid. This pass-through time, for example, may be determined with the aid of a measuring procedure according to the EDANA Standard Test WSP 350.1.R3(12).

For this reason, it is the object of the present invention, to overcome the disadvantages of the prior art mentioned above and to increase the pass-through time for fluid through a tampon.

According to the present invention, this object is achieved by a method of the type mentioned at the outset in that, in step i), the strip made from nonwoven material is positioned in such a manner that it also protrudes over a longitudinal edge of the strip made from absorbent material, a section of the strip made from nonwoven material protruding over the longitudinal edge of the strip made from absorbent material being selected to be of such size that an end face of the roll is completely coverable by the protruding part, and, in a step following step iv), a distal end of the roll, from which the extraction means projects, is, with the exception of one pass-through opening for the extraction means, completely covered by the protruding section of the nonwoven material, and the protruding section of the nonwoven material is connected to form a closed sleeve completely covering, with the exception of the pass-through opening, the distal end, the nonwoven material having a weight per unit area of at least 6 $g/m^2$, in particular between 12 and 30 $g/m^2$, or that, instead of the nonwoven material, a fluid pervious foil made from plastic material is used.

At this point, it shall be noted that, after producing the roll and the sleeve, further steps known per se, for example compressing and pressing with the aid of a press, may follow for the manufacture of the tampon.

The solution according to the present invention allows to completely cover the end at which the extraction means is situated by a nonwoven material. In so doing, it is efficiently inhibited that the wound-up tampon telescopes or pulls apart or that the tampon loses fibers. Furthermore, a protection against fluid leakage is implemented at the distal end. The leakage protection enables to retain the fluid much longer in the tampon than not having a leakage protection. In this way, for example when saturating the tampon by a fluid, the time until the fluid discharges at the distal end is increased by at least 3% vis-a-vis a similar tampon not having a covering. In this instance, EDANA Standard Test WSP 350.1.R3(12) is here preferably used as a measuring method.

Within the present context, a nonwoven material, also referred to as a nonwoven, is understood as a planar textile material, which is produced by applying at least one adhesive onto a fiber mixture or onto a fiber nonwoven made from synthetic and/or natural fibers and by subsequent drying. It is however characterizing for a nonwoven material that the adhesive binds the fibers in the nonwoven material. The nonwoven material is impervious to fibers of the material, from which the absorbent body of the tampon is produced, and it may furthermore be configured in a fluid pervious manner but also in a watertight manner. For example, the nonwoven material may also have the shape of a net or a perforated foil. It shall also be noted at this point that the term nonwoven material is used as a synonym for the term nonwoven.

It is advantageous if the absorbent (fibrous) material is formed by one or a plurality of materials, for example, rayon, cotton, cellulose wadding, tissue laminates, sphagnum, bamboo or chemically enhanced, modified or cross-linked cellulose fibers. This fibrous material has a high hygroscopicity and enables the adhesion of large quantities of fluids to the outside of the fibers and is biologically neutral. It is however also possible to use absorbent (fibrous) materials, which are formed from one or a plurality of the subsequent, synthetic materials, for example, polyester fibers, polyolefin fibers, foamed materials, absorbent sponges, absorbent polymers, capillary channel fibers, synthetic fibers, predominately open-celled flexible polyurethane foam or fibers, or threads made from rayon or formed from a structure type of crystalline modification of cellulose II.

The length of the tampon, for example, may be between 40 mm to 70 mm and have a diameter greater than 11 mm. However, the tampon may also be configured, in particular for the days between the menstrual periods, to have a volume of the absorbent material for the intake of a fluid quantity between 0.5 g and 4 g, preferably 3.5 g, and the absorbent body may have a length of less than 40 mm, preferably have a length between 40 and 10 mm or between 38 and 30 mm.

It is also advantageous if at least the middle part of the absorbent body or an enveloping body enveloping the middle part is cylindrically configured, as a result of which a uniform abutment of the mucous membranes of the vagina may be achieved.

However, it may also be advantageous if at least the middle part of the absorbent body or an enveloping body enveloping the middle part is configured cylindrically or frustoconically because, in so doing, the insertion of the everyday tampon or tampons may be facilitated.

According to another further refinement, it is provided that the cone or the frustum continuously extends from the proximal end to the distal end, and, as a result of which the extraction of the everyday tampon or tampon may be facilitated.

Furthermore, it is however also possible that a core region made from fibrous material is situated at least within the middle part of the absorbent body, which is configured to absorb a smaller fluid quantity for the same volume than the material of the absorbent body. In so doing, the absorption effect or the extent of the fluid intake may, despite the desired greater diameter of the tampon necessary regarding different anatomical features, be more easily adapted, in particular in the absorbent body, to the needed dimensions.

Furthermore, it is however also possible that a core region made from fibrous material is situated at least within the middle part of the absorbent body, which is configured to absorb a smaller fluid quantity for the same volume than the material of the absorbent body, or which is water-repellent. For this reason, the quantity of fluid to subsequently be absorbed may be specified by the design and the volume of the absorbent body.

The tampon, which may be manufactured in different colors, may have markings at its surface. Also, the tampon may be manufactured using a chemical indicator, which changes color for specific illnesses, for example, anemia, diabetes, hepatitis A, B or C and HIV.

An additional improvement may be achieved in that the tampon and/or the absorbent body has a length of less than 40 mm, preferably a length between 40 and 10 mm or between 38 and 30 mm, as a result of which the expansion and the pressure of the tampon against the uterus is also reduced and, for this reason, a sealing and damming of the outlet orifice of the uterus, which can be significantly discomforting, is prevented.

Furthermore, an embodiment is also possible, in which the absorbent body over its total volume is formed from an absorbent material, as a result of which the measurements of the diameter and the quantity of the absorbable fluid may be optimized.

According to a further, advantageous further refinement, it is provided that the absorbent material is formed from a fibrous material, as a result of which the droplets of the fluid may adhere to the individual fibers and a high absorbability of the absorbent body of an everyday tampon or a tampon is achieved.

Advantageous is however also if the absorbent material is formed from a compressed, fibrous material, because the handling of the tampon, in particular inserting and removing the tampon, is thereby facilitated.

A further advantageous further refinement provides that the absorbent body is provided with recesses or grooves extending in the longitudinal direction of the absorbent body, and/or that the recesses or grooves extend in the direction of the longitudinal center axis of the absorbent body in a wave-shaped manner, preferably extending at a consistent height of the amplitude, as a result of which the surface of the tampon is enlarged. For example, an increased absorption of bodily fluid is thereby possible, because the body may discharge different quantities of bodily fluid between successive menstrual periods. Also, these grooves are advantageous for the use of insertion aids for the everyday tampon or tampon.

An even greater surface for the absorption of fluids may be achieved in that the grooves or recesses extend in a spiral-shaped or helical manner.

A further advantage is achieved in that a plurality of grooves or recesses are disposed in the circumferential direction distributed over the absorbent body. In so doing, the surface of the tampon is also enlarged, which results in an increased absorption of bodily fluid, because the body may discharge different quantities of bodily fluid between successive menstrual periods. Women who have an increased discharge are provided with an increased hygiene than is provided by a pantyliner. Also, these grooves are advantageous for the use of insertion aids for an everyday tampon or tampon. The grooves may be produced by pressing the roll in a tampon press.

According to one advantageous embodiment of the present invention, it may be provided that the distal end of the roll, from which the extraction means projects, is covered by the protruding section of the nonwoven material when the extraction means is elongated. This embodiment ensures that the extraction means is positioned outside of the sleeve made from nonwoven material and that it does not impede the production of the sleeve while covering the distal end by the protruding section.

An advantageous further refinement of the present invention is provided in that a circumferential edge region of the protruding section of the strip made from nonwoven material is bent in the direction towards the extraction means for generating the closed sleeve, and sections of the protruding section touching one another are connected to one another.

According to a further variation of the present invention, it may also be provided that the protruding section of the strip made from nonwoven material is, for generating the closed sleeve, connected to a section of the strip made from nonwoven material, which covers the surface shell.

According to a preferred embodiment, the protruding section of the strip made from nonwoven material is connected to the sleeve by welding. Alternatively to welding, other connection methods, for example, adhesive bonding, sewing, etc., may also be used.

Advantageously, the strip made from absorbent material may have a length, the size of which stemming from a value range in which the lower limit is 150 mm and the upper limit is 400 mm, the strip made from nonwoven material having a length, the size of which stemming from a value range in which the lower limit is 50 mm and the upper limit is 250 mm, and the strip made from nonwoven material in step i) is positioned in such a way that it protrudes over the longitudinal edge of the strip made from absorbent material by a length which is substantially equal to a radius or diameter of the roll produced in step iv).

Moreover, it may be provided that the width of the strip made from nonwoven material is greater than the width of the strip made from absorbent material, the strip made from nonwoven material in step i) being positioned on the strip made from absorbent material in such a manner that the strip made from nonwoven material covers at least three quarters of the width of the strip made from absorbent material. In this embodiment of the present invention, the nonwoven material extends over a large portion of the surface shell of the roll. In this manner, it can be ensured that a friction between the mucous membranes of the vagina and the outer surface of the tampon is reduced and a loss of fibers at least in the middle part of the tampon may also be efficiently prevented. Of course, the strip made from nonwoven material may also extend over the total width of the strip made from absorbent material, so that the tampon is completely enclosed by the nonwoven material.

According to an advantageous variation of the present invention, it may be provided that the distal end of the tampon may be coated by a watertight or hydrophobic coating.

A further advantageous embodiment of the present invention is provided in that the distal end of the tampon is provided with a covering made from a watertight or hydrophobic material.

According to the present invention, the aforementioned object may however also be achieved by a tampon of the type mentioned at the outset in that the tampon has a covering in the form of a closed sleeve, made from nonwoven material having a weight per unit area of at least 6 g/m$^2$, in particular between 12 and 30 g/m$^2$, or made from a fluid pervious foil, which, strip or foil, with the exception of a pass-through opening for the extraction means, completely covers at least the distal end, which prevents the escaping of fibers at the distal end, and the covering additionally forming a protection against fluid leakage.

The distal end of the tampon may be protected against undesired fluid entry in that the distal end of the tampon has a watertight or hydrophobic coating.

Moreover, the distal end of the tampon may have a covering made from a watertight or hydrophobic material.

For a better understanding of the present invention, this covering is explained in greater detail on the basis of the subsequent figures.

In respectively greatly simplified illustrations,

FIG. 4 shows a top view of the assembly from FIG. 3;

FIG. 5 shows the assembly from FIG. 3 in a rolled state;

FIG. 6 shows the assembly from FIG. 5 having a distal end closed by the nonwoven material;

FIGS. 7 through 10 show embodiments of a tampon according to the present invention having the distal end coated or covered by a watertight or hydrophobic material.

Figure 1:
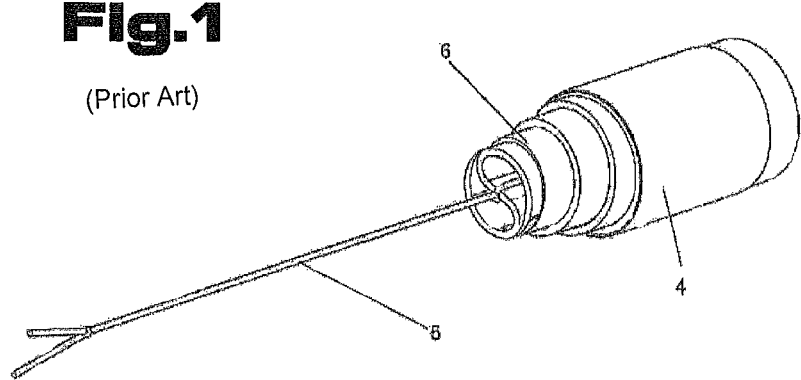
FIG. 1 shows a conventional, rolled tampon telescoping when pulling at the extraction means.

First, it is to be noted that in the differently described embodiments, same parts are provided by the same reference characters or the same component designation, and the disclosures included in the total description may analogously be applied to the same parts having the same reference characters or the same component denotations. The positional information selected in the description, such as top, bottom, lateral, etc. are in reference to the directly described and illustrated figure and this positional information is to be appropriately transferred to the new position when the position is changed.

The exemplary embodiments show possible variant embodiments of the tampon according to the present invention, at this point it being noted that the present invention is not limited to the specifically illustrated variant embodiments of the present invention, but that rather a diverse combination of the individual variant embodiments among one another is also possible and that these possible variations, owing to the technical teachings by the present invention, are part of the technical skill set of those skilled in the arts in this field.

Furthermore, individual features or combinations of features from the shown and described different exemplary embodiments may also illustrate independent, inventive solutions or solutions according to the present invention.

The object underlying the individual inventive solutions may be concluded from the description.

All information regarding value ranges in the present description are to be understood in such a way that these value ranges include any and all subranges, for example, the specification 1 through 10 is to be understood in such a way that all subranges, starting from the lower limit 1 to the upper limit 10 are included, that is, all subranges starting at a lower limit 1 or greater and ending at an upper limit 10 or less, for example, 1 through 1.7, or 3.2 through 8.1, or 5.5 through 10.

Figure 2:
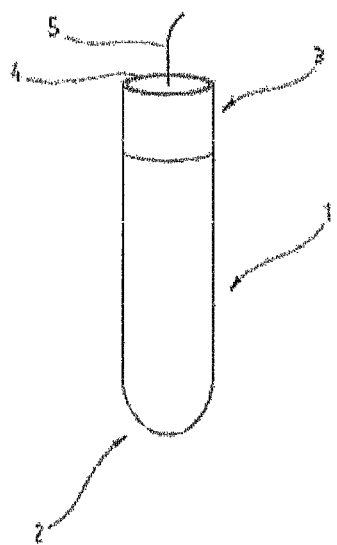
FIG. 2 shows a perspective view of a tampon according to the present invention.

According to FIG. 2, a tampon 1 according to the present invention includes an absorbent body made from an absorbent material 6, for example absorbent cotton. Tampon 1 has a proximal end 2 and a distal end 3 and a middle part extending between proximal end 2 and distal end 3. It is advantageous if tampon 1 at proximal end 2 is configured in a rounded or beveled manner.

An extraction means 5 connected to the absorbent body is situated at distal end 3. A covering made from a strip 4 of a nonwoven material completely covering, with the exception of a pass-through opening for extraction means 5, denoted by reference character 13 in FIG. 6, distal end 3 is disposed at its distal end 3. Preferably, pass-through opening 13 has a diameter which is substantially equal to a diameter of extraction means 5. The covering prevents a telescoping of the tampon and that fibers escape at distal end 3. In this way, FIG. 1 in an exemplary manner illustrates how a conventional tampon may be drawn apart (telescoped) when pulling at extraction means 5. In this instance, a winding of a strip 6 made from an absorbent material, which is connected to extraction means 5, is drawn apart in the longitudinal direction, as a result of which conventional tampons may unravel.

The middle part of tampon 1 may be cylindrically configured. It is however also possible that at least the middle part is frustoconically configured. The cylinder or cone or frustum may however also extend continuously from the proximal end to the distal end. For all mentioned spatial shapes of tampon 1, any cross-sectional changes over the length of tampon 1 are possible, for example, a wave-shaped contour or recesses extending at least over a portion of the circumference and/or in the longitudinal direction.

A further advantageous embodiment provides that at least the middle part of tampon 1 is provided with recesses or grooves extending in the longitudinal direction of the middle part, and/or that the recesses or grooves extend in the direction of the longitudinal center axis of tampon 1 in a wave-shaped manner, preferably extending at a consistent height of the amplitude, as a result of which the surface of tampon 1 is enlarged, making an increased absorption of bodily fluid possible. An even greater surface for the absorption of fluid may be achieved in that the grooves or recesses extend in a spiral-shaped or helical manner.

Figure 3:
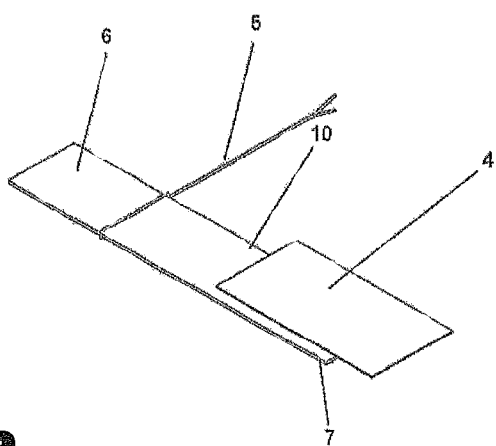
FIG. 3 shows a perspective view of an assembly of an absorbent material and a nonwoven material according to the manufacturing steps for the manufacture of the tampon from FIG. 2.

In a method according to the present invention for the manufacture of tampon 1 shown in FIG. 2, according to FIGS. 3 and 4, strip 4 made from nonwoven material is positioned on a strip 6 made from an absorbent material, a part 8 of strip 4 protruding over a narrow side 7 of strip 6 made from absorbent material. Furthermore, strip 4 is positioned on strip 6 in such a way that it also protrudes over a longitudinal edge 10 of strip 6. A section 11 of strip 4 protruding over longitudinal edge 10 of strip 6, in this instance, is selected to be of such size that, after rolling up strips 4 and 6 into a roll 9, an end face 12 of this roll 9 may be completely covered by protruding section 11, as it is shown in FIGS. 5 and 6. In this instance, the used nonwoven material has a weight per unit area of at least 6 g/m$^2$, in particular however between 12 and 30 g/m$^2$. Instead of the nonwoven material, a fluid pervious foil made from plastic material may be used. The foil may be rendered fluid pervious, for example, by inserting perforations.

The absorbent construction of strip 6 may be produced in a plurality of sizes and shapes and from a plurality of fluid-absorbent materials.

Of course, it is desirable that absorbent materials are used, which include a minimum content of soluble foreign materials because the product remains in the body for a certain amount of time. Retained soluble foreign materials could pose a safety risk if toxic, irritant or cause sensitivity.

A list of useable materials includes materials including cellulose, for example, rayon, cotton, cellulose, cellulose wadding, tissue laminates, sphagnum, bamboo and chemically reinforced, modified or cross-linked cellulose fibers; synthetic materials, for example, polyester fibers, polyolefin fibers, absorbent foams, for example an elastically resilient polyurethane foam, absorbent sponges, extremely absorbent polymers, absorbent gel-forming materials, processed fibers, such as capillary channel fibers and fibers having several members, for example; and synthetic fibers or an equivalent material or combinations of materials or mixtures thereof.

If using such synthetic foams, it is also possible, for example by setting a specific temperature for the manufacture of the absorbent body, to partially close the outer skin, that is, to achieve a closed skin in the external region owing to a partial temperature effect. In so doing, an escaping of fluid absorbed in the foam structure is additionally made more difficult or is prevented. Such a configuration may be advantageous, in particular in the proximal end region 4 of tampon 1.

Within the scope of the present invention, the manufacture of tampon 1 may be carried out by a broad range of materials which maintain, under the conditions prevailing in the region of the vagina and the uterus, that is, at body temperatures a pH value of approximately 4, their condition over a longer period of time, and which do not give off toxic substances or solutions damaging to the mucous membranes or the like. Advantageously, materials such as flexible polyurethane foams having a very low volumetric weight and a predominantly open-celled structure may be used for strip 6. Using a more absorbent material further reduces the risk of leaking fluid. Another advantage of such foamed structures is that the open cells in the delivered state or before being introduced into the vagina can be filled with medicaments or lubricants which can be discharged to the mucous membranes of the vagina and uterus when inserted.

Furthermore, it is advantageous if the materials used for the nonwoven material are bio-degradable and, for example, are made from PLA or other bio-degradable plastic materials or plastic compounds and/or from filaments or fibers made from or recycled from plastic materials, such as R-PP, R-PET or the like, and optionally are formed from these materials in different mixtures or as multi-layered parts.

Preferably, strip 6 has a length 1, the size of which stemming from a value range, which has a lower limit of 150 mm and an upper limit of 400 mm. Strip 4 has a length c, the size of which stemming from a value range, which has a lower limit of 50 mm and an upper limit of 250 mm Preferably, strip 4 is positioned in such a way that it protrudes over longitudinal edge 10 of strip 6 at least by a width b, which substantially equates to the radius of roll 9.

According to a preferred embodiment, strip 6 has a length 1 of 255 mm, part 8 having a length a of 30 mm and strip 4 having a total length c of 127 mm. In this instance, section 11 has a width b of 30 mm.

Moreover, a total width of strip 4 may be greater than a total width of strip 6. Particularly preferably, strip 4 is positioned on strip 6 in such a manner that strip 4 extends over at least three quarters of the width of strip 6, as it is shown in FIGS. 3 and 4.

After positioning strip 4 on strip 6, strip 4 is connected to strip 6. The connection of strips 4 and 6 may be carried out, for example, by welding, adhesive bonding, sewing or any other form suitable for connecting.

In a further step, an extraction means 5, for example a filament or a string, is attached to strip 6 made from absorbent material. Preferably, strip 6 is looped by extraction means 5, as it is shown in FIGS. 2 and 3. Then, strips 4 and 6 are wound onto roll 9. In this instance, the direction of winding is selected in such a manner that strip 4 covers a section of a surface shell of roll 9, such as it is, for example, shown in FIG. 5.

Protruding part 8 of strip 4 is, by a section 15 of strip 4 connected to a strip 6, connected into a closed ring, for example, by welding and/or adhesive bonding and/or sewing.

A distal end of roll 9, from which extraction means 5 projects, is, with the exception of pass-through opening 13 for extraction means 5, completely covered by protruding section 11 of strip 4. Subsequently, protruding section 11 of strip 4 is connected to form a closed sleeve completely covering the distal end, except for pass-through opening 13.

Particularly preferably, covering the distal end of roll 9 by protruding section 11 of strip 4 occurs while the extraction means 5 is elongated. Covering the distal end of roll 9 may be carried out by bending or folding a circumferential edge region 14 of protruding section 11 in the direction towards the elongated extraction means 5, and pass-through opening 13 is left unobstructed or the extraction means, before being folded on the end face of the roll, is passed through protruding section 11. This, for example, may be carried out with the aid of a needle, to which the extraction means is fastened. Sections of protruding section 11 touching one another then may be connected to one another, for example by welding, sewing or adhesive bonding so that a closed covering results. In this embodiment, it is advantageous if section 11 is at least approximately equal to a radius of roll 9.

Alternatively or additionally to the variation mentioned in the last paragraph, section 11 of strip 4 for generating the closed sleeve could also be connected to section 15 made from nonwoven material, which is situated at the surface shell of the roll. If width b of section 11 is slightly greater than the diameter of roll 9, an area of section 11 may be folded over entire distal end face 12 of roll 9 and be connected to section 15. In so doing, it has been proven to be advantageous if the part of section 11 folded over the end face of roll 9 has an opening, for example in the form of a slot, for passing through extraction means 5.

Roll 9 shown in FIG. 6, which has the covering of the distal end in the form of a closed sleeve made from a nonwoven or from nonwoven material 4 represents a preform, which subsequently is, in the manufacturing steps known per se, for example pressing and compacting in a press, further processed into tampon 1, as shown in FIG. 2. Alternatively or additionally to covering the distal end by a nonwoven material, the distal end may also be covered by a fluid pervious foil made from plastic material. Covering the distal end implements a leakage protection.

In this way, a tampon according to the present invention has a significantly greater pass-through time for a fluid than a conventional tampon has. In Table 1, results for the tampon, determined according to the EDANA Standard Test WSP 350.1.R3(12), are compared to one another having or not having a covering at the distal end. The same test requirements were selected for all tampons to produce comparable findings. In this test, the time until the first drop of the test fluid, the so-called Syngina fluid, reaches the ground, was measured.

TABLE 1

|  | Nonwoven 14 g/m$^2$ | Nonwoven 12 g/m$^2$ |
|---|---|---|
| With covering | Means: 14 min 59 sec. | Means: 15 min. 48 sec. |
| Without covering | Means: 13 min 46 sec. | Means: 15 min. 02 sec. |
| Improvement of the leakage protection as a percentage | 8.84% | 5.1 % |

According to FIG. 7, tampon 1 at its distal end may be provided with a watertight or hydrophobic coating 16. Coating 16 may be implemented by dampening or soaking the distal end of tampon 1 using an impregnation liquid, for example, a lacquer, wax, resin, etc.

As shown in FIG. 7, coating 16 may completely cover the distal end, or, as shown in FIG. 8, partially cover the distal end. In FIG. 8, the coating is denoted by reference character 17. The coating of tampon 1 by watertight or hydrophobic coating 16, 17 may be carried out independently from the other manufacturing steps of tampon 1 and individually constitute the subject of an invention.

According to FIG. 9, the distal end may also be formed using a covering 18 made from a water impervious or hydrophobic material. As shown in FIG. 9, covering 18 may be manufactured as a sleeve, which also includes the side areas of tampon 1; however, the greater part of the side areas of the tampon are not covered.

According to FIG. 10, covering 19 made from water impervious or hydrophobic material may also only cover the distal end without including the side areas of tampon 1. In this case, covering 19 is implemented as a disk.

It is advantageous if the materials used for coverings 18, 19 are bio-degradable and, for example, are formed from PLA or other bio-degradable plastic materials or plastic compounds and/or from filaments or fibers made from or recycled from plastic materials, such as R-PP, R-PET or the like, and optionally are formed from these materials in different mixtures or as multi-layered parts.

Providing tampon 1 with watertight or hydrophobic coverings 18 and 19 also may be carried out independently from the other manufacturing steps of tampon 1 and individually constitute the subject of an invention.

Coverings 18, 19 may be directly applied to strip 4 (for example by welding, adhesive bonding or sewing). Strip 4 may be applied before or after step i).

For the record, in conclusion it is to be noted that, for a better understanding of the composition of the tampon, the tampon or its components are in part illustrated in a manner not to scale and/or in an enlarged and/or reduced manner.

LIST OF REFERENCE CHARACTERS 1 tampon
2 proximal end
3 distal end
4 strip made from nonwoven material
5 extraction means
6 strip made from absorbent material
7 narrow side
8 part of the strip made from nonwoven material
9 roll
10 longitudinal edge
11 protruding section
12 end face of the roll
13 pass-through opening
14 edge region
15 section of the strip made from nonwoven material
16 coating
17 coating
18 covering
19 covering
a length
b width
c total length
l length

What is claimed is:

1. A method for the manufacture of a tampon, comprising the following steps:
   i) positioning of a first strip made from a nonwoven material having a weight per unit area of at least 6 g/m$^2$ or a liquid-permeable film of plastic on a second strip of an absorbent material, so that a protruding part of the first strip protrudes over a narrow side of the second strip made from absorbent material,
   ii) connecting the first strip to the second strip made from absorbent material,
   iii) situating an extraction means comprising a filament or a string at the second strip made from absorbent material,
   iv) rolling up the second strip made from absorbent material and the first strip into a roll, in which the first strip covers at least a section of a surface shell of the roll,
   (v) connecting the protruding part of the first strip to a section of the first strip that is connected to the second strip made from absorbent material,
   wherein,
   in step i), the first strip is positioned in such a manner that the first strip also protrudes over a longitudinal edge of the second strip made from absorbent material, wherein a protruding section of the first strip protruding over the longitudinal edge of the second strip made from absorbent material is selected to be of such size that an end face of the roll is completely coverable by the protruding section, and,
   in a step following step iv), a distal end of the roll, from which the extraction means projects, is, with the exception of a pass-through opening for the extraction means, completely covered by the protruding section of the first strip, and the protruding section of the first strip is connected to form a closed sleeve completely covering, with the exception of the pass-through opening, the distal end, wherein the second strip made from absorbent material has a length, the size of which stemming from a value range in which its lower limit is 150 mm and its upper limit is 400 mm, wherein the first strip has a length, the size of which stemming from a value range in which its lower limit is 50 mm and its upper limit is 250 mm, and wherein the first strip in step i) is positioned in such a way that the first strip protrudes over the longitudinal edge of the second strip made from absorbent material by a width which is substantially equal to a radius of the roll produced in step iv).

2. The method as recited in claim 1, wherein the distal end of the roll, from which the extraction means projects, is covered by the protruding section of the first strip while the extraction means is elongated.

3. The method as recited in claim 1, wherein a circumferential edge region of the protruding section of the first strip is bent in the direction towards the extraction means for generating the closed sleeve, and wherein sections of the protruding section touching one another are connected to one another.

4. The method as recited in claim 1, wherein the protruding section of the first strip is, for generating the closed sleeve, connected to a section of the first strip that covers the surface shell.

5. The method as recited in claim 1, wherein the protruding section of first strip is connected to the closed sleeve by welding.

6. The method as recited in claim 1, wherein the width of the first strip is greater than the width of the second strip made from absorbent material, wherein the first strip in step i) is positioned on the second strip absorbent material in such a manner that the first strip covers at least three quarters of the width of the second strip absorbent material.

7. The method as recited in claim 1, wherein the distal end of the tampon is provided with a watertight or hydrophobic coating.

8. The method as recited in claim 1, wherein the distal end of the tampon is provided with a covering made from a watertight or hydrophobic material.

* * * * *